(12) United States Patent
Terasawa et al.

(10) Patent No.: US 9,063,098 B2
(45) Date of Patent: Jun. 23, 2015

(54) METHOD OF INSPECTING MASK, MASK INSPECTION DEVICE, AND METHOD OF MANUFACTURING MASK

(75) Inventors: Tsuneo Terasawa, Kanagawa (JP); Osamu Suga, Kanagawa (JP)

(73) Assignee: Renesas Electronics Corporation, Kawasaki-shi (JP)

( * ) Notice: Subject to any disclaimer, the term of this patent is extended or adjusted under 35 U.S.C. 154(b) by 117 days.

(21) Appl. No.: 13/549,482

(22) Filed: Jul. 15, 2012

(65) Prior Publication Data

US 2013/0017475 A1    Jan. 17, 2013

(30) Foreign Application Priority Data

Jul. 15, 2011    (JP) .................................. 2011-156288

(51) Int. Cl.
*G03F 1/84*    (2012.01)
*G01N 21/88*    (2006.01)
*G01N 21/956*    (2006.01)

(52) U.S. Cl.
CPC .......... *G01N 21/956* (2013.01); *G01N 21/8806* (2013.01); *G01N 2021/8822* (2013.01); *G01N 2021/95676* (2013.01); *G03F 1/84* (2013.01)

(58) Field of Classification Search
CPC ............ G01N 2021/8822; G01N 2021/95676; G01N 21/8806; G01N 21/9501; G01N 21/956; G03F 1/22; G03F 1/24; G03F 1/84
See application file for complete search history.

(56) References Cited

U.S. PATENT DOCUMENTS

| 6,235,434 | B1 | 5/2001 | Sweeney et al. |
| 2003/0067598 | A1 | 4/2003 | Tomic |
| 2007/0188743 | A1 | 8/2007 | Tanaka et al. |

FOREIGN PATENT DOCUMENTS

| JP | 2002-532738 A | 10/2002 |
| JP | 2003-114200 A | 4/2003 |
| JP | 2007-158828 A | 6/2007 |
| JP | 2007-219130 A | 8/2007 |

OTHER PUBLICATIONS

Isao Tanabe et al. "Introduction to Photomask Technology", Kogyo Chousakai Publishing Co., Ltd., Dec. 2006, pp. 266-268.

*Primary Examiner* — Mark R Gaworecki
(74) *Attorney, Agent, or Firm* — Miles & Stockbridge P.C.

(57) ABSTRACT

There is provided a method of high-sensitively detecting both of a phase defect existing in a mask blank and a phase defect remaining after manufacturing an EUVL mask. When the mask blank is inspected, EUV light having illumination NA to be within an inner NA but a larger value is irradiated. When the EUVL mask is inspected, by using a dark-field imaging optical system including a center shielding portion for shielding EUV light and a linear shielding portion for shielding the EUV light whose width is smaller than a diameter of the center shielding portion, the center shielding portion and the linear shielding portion being included in a pupil plane, the EUV light having illumination NA as large as or smaller than the width of the linear shielding portion is irradiated.

4 Claims, 12 Drawing Sheets

Y DIRECTION
X DIRECTION

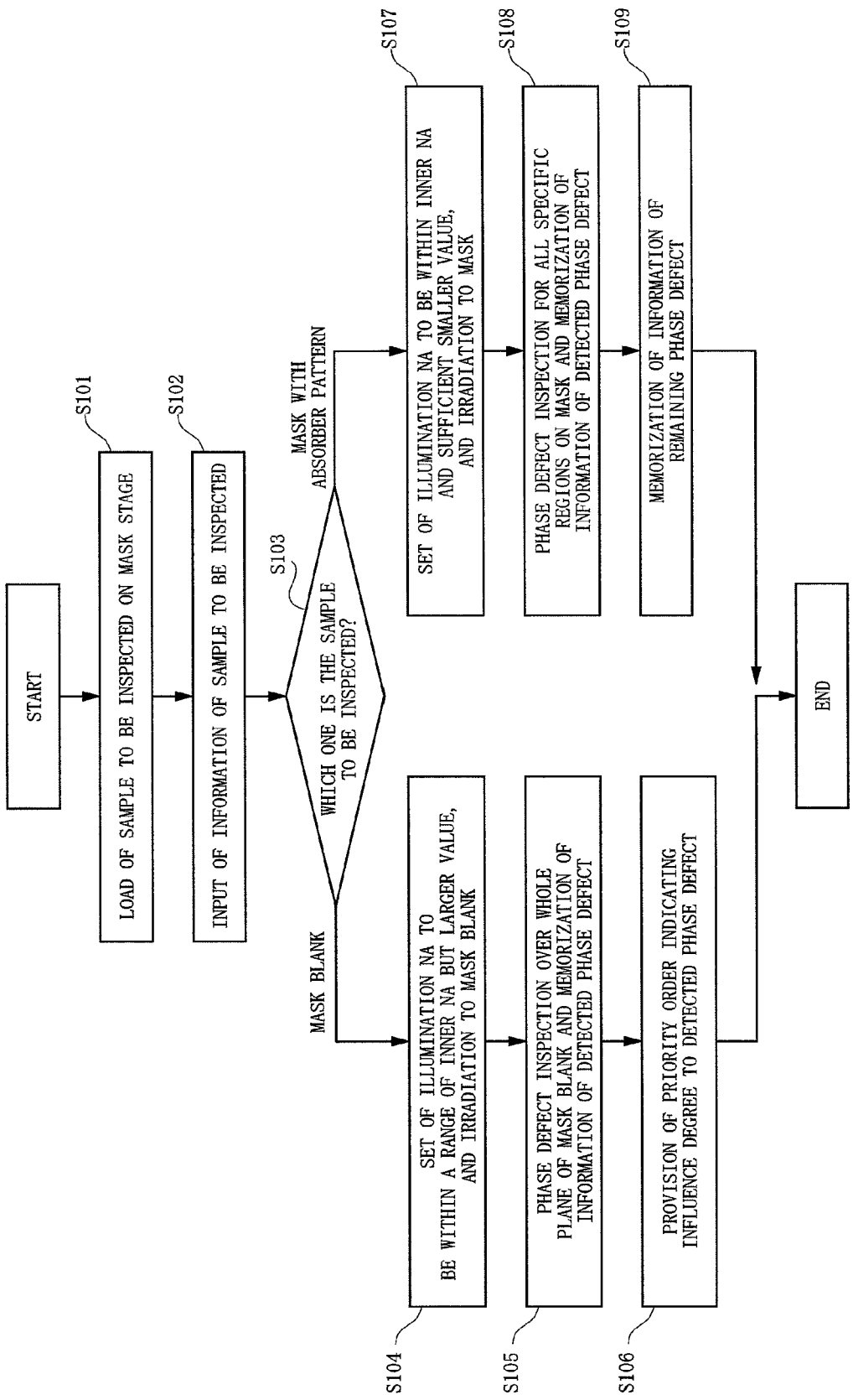

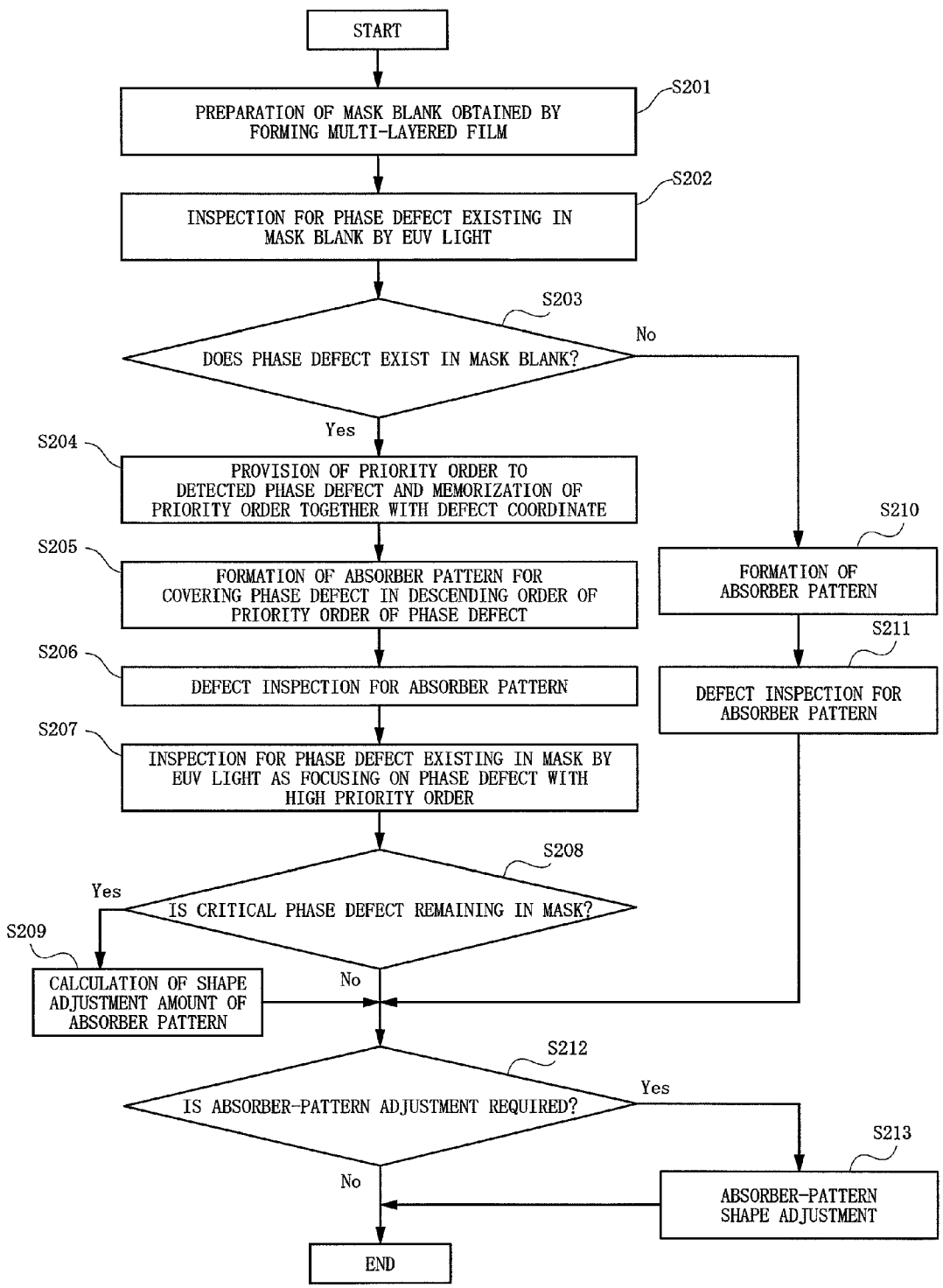

METHOD OF INSPECTING MASK, MASK INSPECTION DEVICE, AND METHOD OF MANUFACTURING MASK

CROSS-REFERENCE TO RELATED APPLICATION

The present application claims priority from Japanese Patent Application No. 2011-156288 filed on Jul. 15, 2011, the content of which is hereby incorporated by reference into this application.

TECHNICAL FIELD OF THE INVENTION

The present invention relates to a technique of manufacturing a lithography mask used for forming a circuit pattern of a semiconductor device. More particularly, the present invention relates to a technique effectively applied to a method of inspecting a mask for extreme ultra-violet ray exposure, a mask inspection device, and a method of manufacturing the mask, the mask being used for a lithography process using so-called extreme ultra-violet ray (EUV light) exposure whose wavelength is about 10 to 15 nm.

BACKGROUND OF THE INVENTION

A semiconductor device (semiconductor integrated circuit device) is produced by repeatedly using photolithography in which exposure light is irradiated onto a mask of an original plate, on which a circuit pattern is drawn, so as to transfer the circuit pattern on a main plane of a semiconductor substrate (hereinafter, referred to as wafer) through a reduced projection optical system.

However, in recent years, in response to demand for microfabrication of the semiconductor device, development of EUV lithography (hereinafter, referred to as EUVL) using EUV light whose wavelength is shorter than that of the light used for the exposure of the photolithography has been advanced. By using this EUVL, resolution can be improved, and a further-microfabricated circuit pattern can be transferred.

In a wavelength range of the EUV light (whose center wavelength is, for example, 13.5 nm), a transparency mask cannot be used because of light absorption of its material. Therefore, a multi-layered reflection substrate which utilizes reflection by a multi-layered film made of molybdenum (Mo), silicon (Si), and others, is used as an EUVL mask blank (hereinafter, referred to as mask blank). An EUVL mask is configured by forming an absorber pattern on a plane of this mask blank (see in, for example, "Introduction to Photomask Technology", Kogyo Chousakai Publishing Co., Ltd., written by Isao TANABE, Yohichi TAKEHANA, and Morihisa HOUGA, published on December 2006, pp. 266 to 268 (Non-Patent Document 1)).

Also, since a transparent lens cannot be used, reflection-type exposure optical system (reflection-type imaging optical system, EUV optical system) made of only a reflection plane of a multi-layered film obtained by alternately stacking Molybdenum (Mo) and silicon (Si) is used for the reduced projection optical system as described in, for example, Japanese Patent Application Laid-Open Publication No. 2007-158828 (Patent Document 1). The light from a light source is homogenized through a reflection-type illumination optical system, and is irradiated to the EUVL mask. The light irradiated to the EUVL mask reflects on the EUVL mask, and reaches the wafer through a reflection-type projection optical system, so that the absorber pattern of the EUVL mask is projected on the main plane of the wafer.

In the EUVL, even when slight height abnormality of about several nm occurs in the plane of the mask blank, the height abnormality results in large change in phase of the EUV reflection light, and results in defects such as dimensional change or failure of resolution in the transfer of the absorber pattern onto the main plane of the wafer. Such a defect which results in the phase change is called phase defect. Accordingly, it is required to detect the phase defect at a stage of a mask blank obtained prior to coating of the absorber pattern.

As a general method of inspecting the mask blank, there are a method of detecting a foreign material and a method of detecting a bright-field image (microscope image) from diffused reflection light caused by irradiating laser light to the mask blank. However, the influence of the phase defect also depends on an internal structure of the multi-layered film, and therefore, it is considered that an inspection method at wavelength (the same wavelength) of detecting the defect with using detection light whose wavelength is the same as that of the EUV light used for the exposure is suitable. As one example of this method, for example, Japanese Patent Application Laid-Open Publication No. 2003-114200 (Patent Document 2) discloses a method with using a dark-field image inspection image. Also, for example, Japanese Patent Application Laid-Open Publication No. 2007-219130 (Patent Document 3) discloses an inspection method of differentiating concavity and convexity of a plane of the phase defect. Further, for example, Japanese Patent Application Laid-Open Publication (Translation of PCT Application) No. 2002-532738 (Patent Document 4) discloses a technique of improving a projection image in pattern transfer by an exposure device by adjusting a contour of the absorber pattern if the absorber pattern is formed in a state that the phase defect already exists.

SUMMARY OF THE INVENTION

In the dark-field inspection method with using the EUV light in the above-described Patent Document 2, the phase defect of the mask blank can be high-sensitively detected as a bright point. Further, the document discloses that a shielding portion having a predetermined shape is additionally provided to an inspection optical system when an EUVL mask having an absorber pattern is inspected in order to avoid influence of a diffracted-light component which is a cause of increasing a background level of an inspection signal. However, the additional provision of the shielding portion causes a risk that a transparent amount of scattered light caused by the phase defect is reduced, which results in reduction of detection sensitivity for the phase defect.

Also, in the inspection method in the above-described Patent Document 3, presence/absence of defects in the plane of the mask blank and the differentiation of the concavity and convexity therein can be judged. However, there is no consideration of the influence of the diffracted light caused when the EUVL mask having the absorber pattern is inspected.

Meanwhile, the inspection method in the above-described Patent Document 4 discloses a method by which the EUVL mask can be handled as a non-defective product even when the phase defect remains after forming the absorber pattern. However, the document does not describe a method of inspecting the phase defect remaining after forming the absorber pattern.

As described above, even in any inspection method described above, it is difficult to high-sensitively detect both of the phase defect remaining in the mask blank and the phase defect substantially remaining after manufacturing the EUVL mask.

Also, when the phase defect of the multi-layered film which is difficult to be adjusted is detected, a process does not proceed to a step of forming the absorber pattern even if the defect is a micro-size defect, and the mask blank is handled as a defective product and is discarded. According to consideration of the present inventors, if the phase defect is at a position covered by the formed absorber pattern, the mask blank is available. However, depending on a total number of the detected phase defects, it is difficult to cover all the phase defects, and therefore, it is required to specify a defect not covered thereby and remaining in the EUVL mask. Eventually, although it is required to detect the phase defect so as to avoid the influence of the diffracted light of the absorber pattern, it is difficult to high-sensitively perform the detection as described above.

A preferred aim of the present invention is to provide a method of high-sensitively detecting both of a phase defect remaining in a mask blank and a phase defect remaining after manufacturing an EUVL mask.

Also, another preferred aim of the present invention is to provide a defect inspection device of high-sensitively detecting both of a phase defect remaining in a mask blank and a phase defect remaining after manufacturing an EUVL mask.

Further, still another preferred aim of the present invention is to provide a method of manufacturing an EUVL mask capable of removing a critical phase defect remaining in the EUVL mask by detecting those of a mask blank and the EUVL mask by the same defect inspection device.

The above and other preferred aims and novel characteristics of the present invention will be apparent from the description of the present specification and the accompanying drawings.

The typical embodiments of the inventions disclosed in the present application will be briefly described as follows.

This embodiment is a method of inspecting an EUVL mask, and the method includes: a step of irradiating EUV light to a mask; a step of imaging the EUV light which reflects from the mask onto a light-receiving plane of an image detector through a dark-field imaging optical system; and a step of detecting a detection signal of a phase defect existing in the mask from detection signals obtained by the image detector. When the EUV light is irradiated to the mask, illumination NA (numerical aperture) of the EUV light is changed depending on a case that the absorber pattern exists in the mask and a case that the absorber pattern does not exist in the mask.

Also, this embodiment is an inspection device for an EUVL mask, and the inspection device includes: a stage movable in X and Y directions on which the EUVL mask is loaded; a light source of generating EUV light; an illumination optical system of irradiating the EUV light to the EUVL mask; illumination aperture of changing illumination NA (numerical aperture) when the EUV light is irradiated to the EUVL mask; a dark-field imaging optical system of collecting scattered light caused from the mask to form a dark-field inspection image; an image detector of acquiring the dark-field inspection image as a pixel signal; and an aperture driving unit of adjusting the illumination aperture based on information of an absorber pattern.

Further, this embodiment is a method of manufacturing an EUVL mask, and the method includes: (a) a step of preparing a mask blank, on which a multi-layered film for reflecting EUV light is formed, on a main plane of a substrate; (b) a step of irradiating the EUV light to the mask blank to detect a phase defect of the mask blank; (c) a step of memorizing a positional coordinate of the phase defect detected in the step of (b) and of providing a priority order, which indicates a degree of influence on pattern transfer, to the phase defect; (d) a step of forming an absorber pattern on the multi-layered film of the mask blank as covering the phase defect of the mask blank in descending order of the priority for forming the mask; and (e) a step of detecting the phase defect of the mask by an inspection device with using the EUV light as an inspection light.

The effects obtained by typical embodiments of the present invention disclosed in the present application will be briefly described below.

A method of high-sensitively detecting both of a phase defect remaining in a mask blank and a phase defect remaining after manufacturing an EUVL mask can be provided.

Also, a defect inspection device of high-sensitively detecting both of the phase defect remaining in the mask blank and the phase defect remaining after manufacturing the EUVL mask can be provided.

Further, a method of manufacturing the EUVL mask capable of removing a critical phase defect remaining in the EUVL mask by detecting those of the mask blank and the EUVL mask by the same defect inspection device can be provided.

BRIEF DESCRIPTIONS OF THE DRAWINGS

Figure 5A:
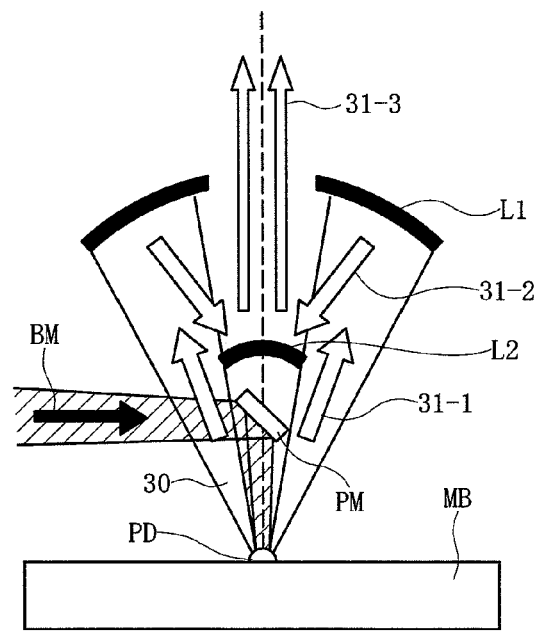
FIG. 5A is a diagram explaining a relationship between a dark-field inspection image obtained when the phase defect remains in the mask blank and scattered light passing through a pupil plane of a Schwarzschild optical system according to the first embodiment of the present invention, and is an enlarged diagram of a part including a dark-field imaging optical system and the mask blank.
Figure 5B:
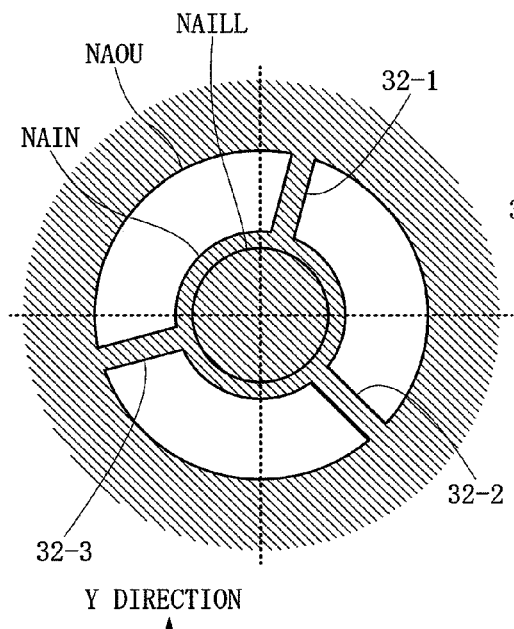
FIG. 5B is a diagram explaining a relationship between a dark-field inspection image obtained when the phase defect remains in the mask blank and scattered light passing through a pupil plane of a Schwarzschild optical system according to the first embodiment of the present invention, and is a schematic diagram illustrating a pupil plane of a dark-field imaging optical system.
Figure 5C:
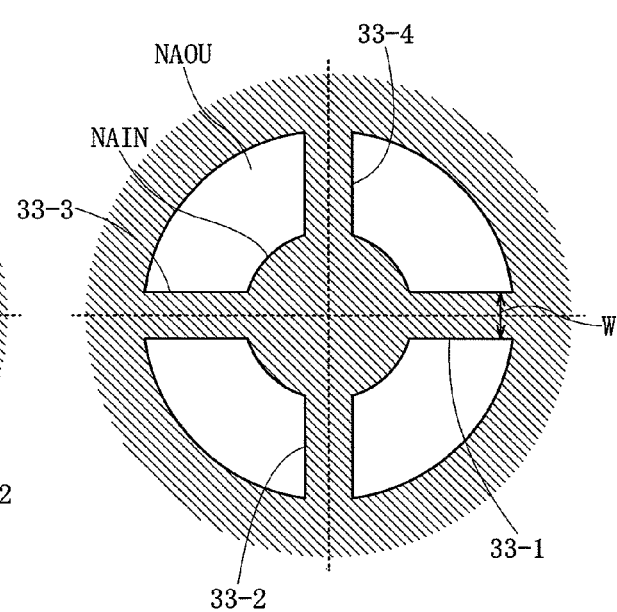
Figure 6A:
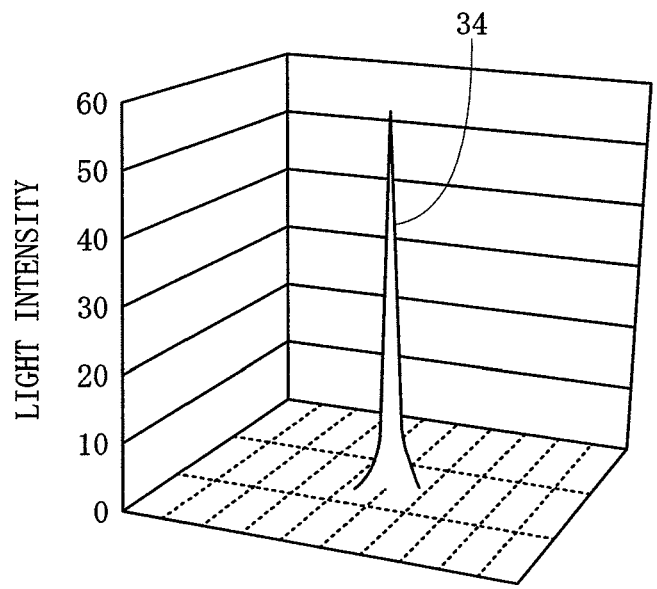
Figure 6B:
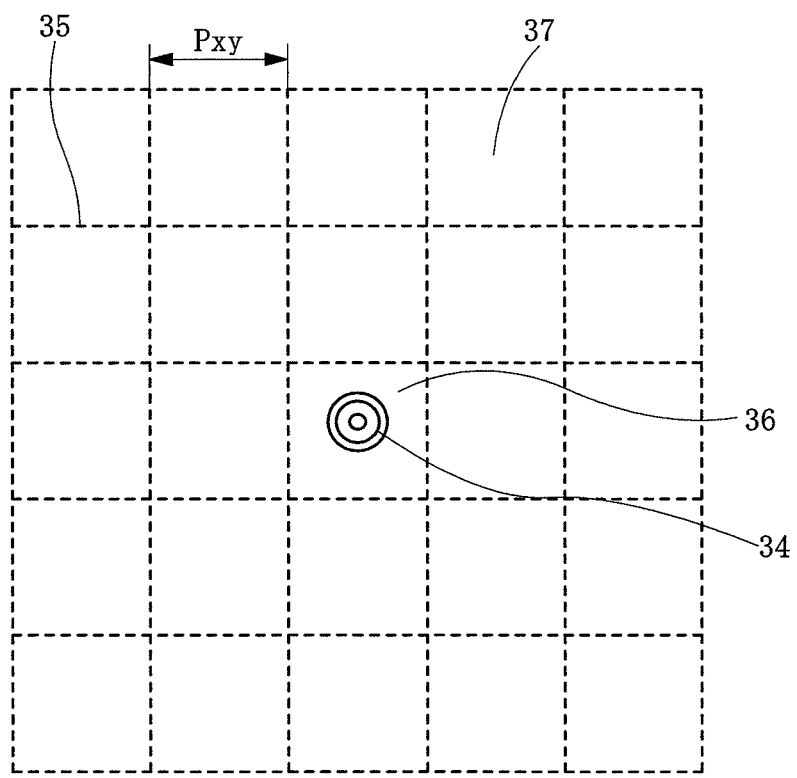
Figure 7A:
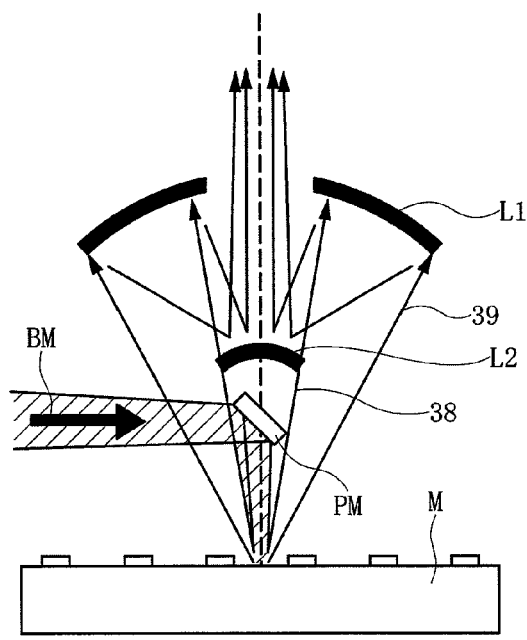
Figure 7B:
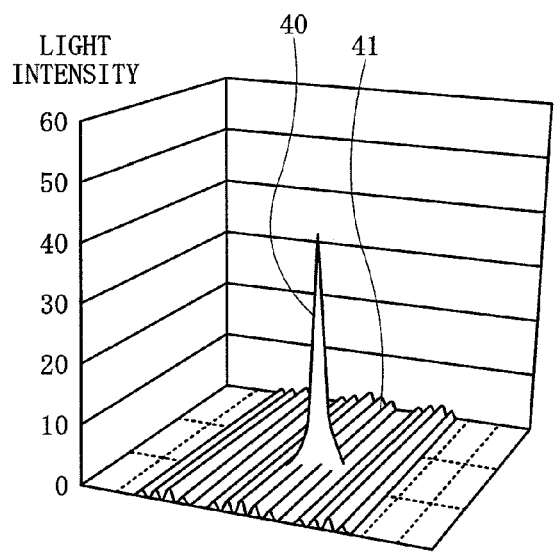
Figure 7C:
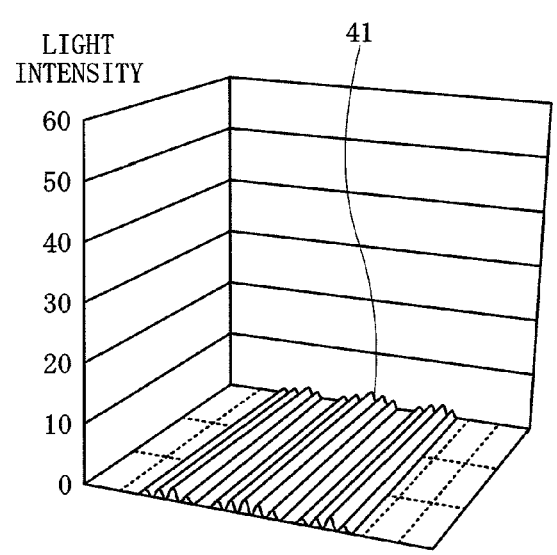
Figure 8A:
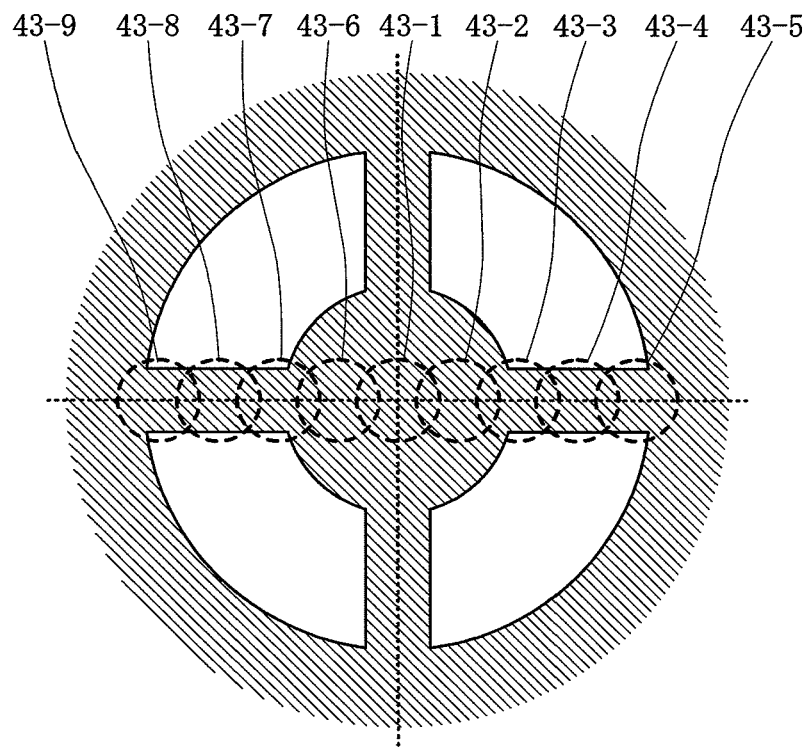
Figure 8B:
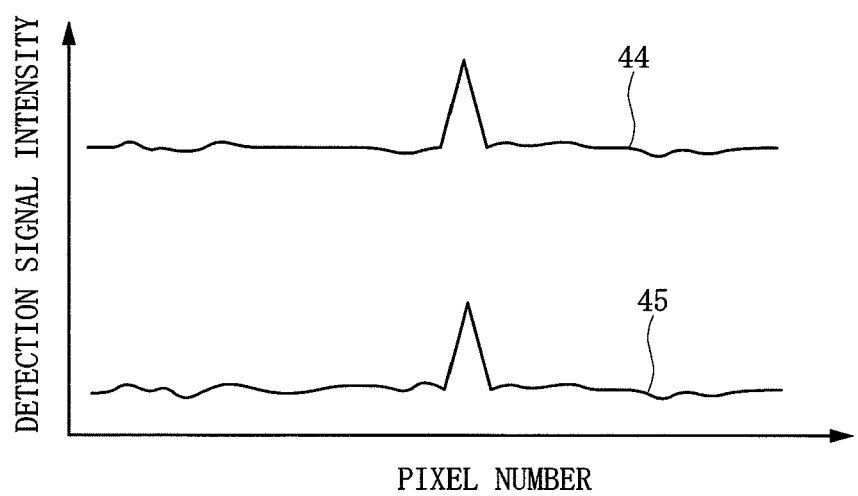
Figure 10:
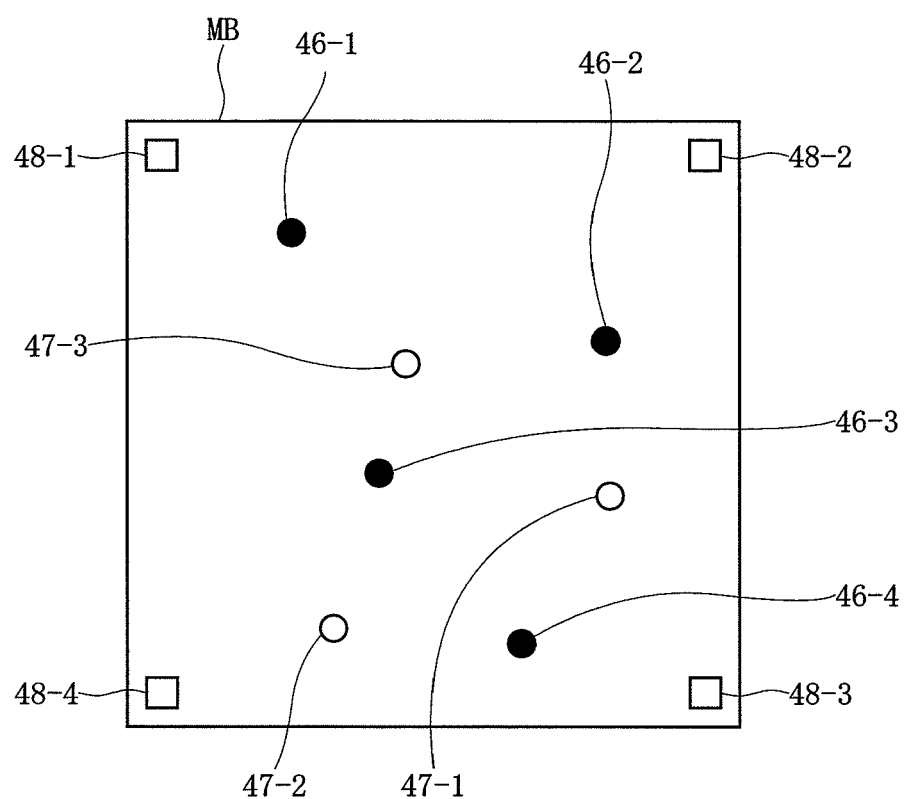
Figure 11A:
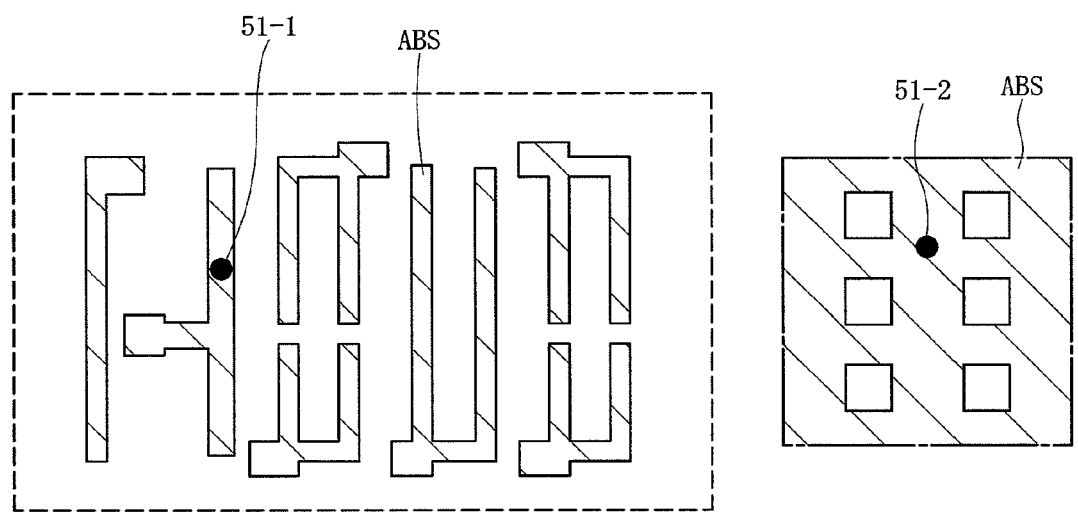
Figure 11B:
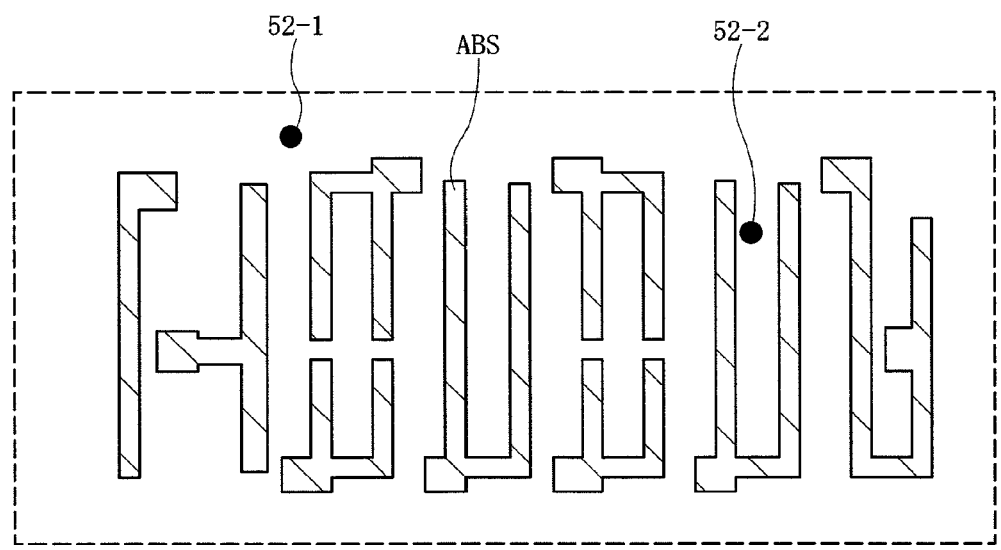

FIG. 5C is a diagram explaining a relationship between a dark-field inspection image obtained when the phase defect remains in the mask blank and scattered light passing through a pupil plane of a Schwarzschild optical system according to the first embodiment of the present invention, and is a schematic diagram illustrating a pupil plane of a dark-field imaging optical system including linear shielding portions;

FIG. 6A is a diagram explaining a result obtained by observing the phase defect remaining in the mask blank with using the dark-field imaging optical system according to the first embodiment of the present invention, and is a diagram illustrating light-intensity distribution of a dark-field inspection image in a region where the phase defect exists;

FIG. 6B is a diagram explaining a result obtained by observing the phase defect remaining in the mask blank with using the dark-field imaging optical system according to the first embodiment of the present invention, and is a diagram explaining a relationship between pixel and a dark-field inspection image of a phase defect which is imaged on a light-receiving plane of a two-dimensional array sensor;

FIG. 7A is a diagram explaining a result obtained by observing a phase defect existing between absorber patterns adjacent to each other in observation of the EUVL mask having the absorber pattern according to the first embodiment of the present invention, and is an enlarged diagram of a part including the dark-field imaging optical system and the mask blank (diagram explaining a relationship between the dark-field imaging optical system and the EUV light diffracted from the absorber pattern);

FIG. 7B is a diagram explaining a result obtained by observing a phase defect existing between absorber patterns adjacent to each other in observation of the EUVL mask having the absorber pattern according to the first embodiment of the present invention, and is a diagram illustrating light-intensity distribution of a dark-field inspection image in the region where the phase defect exists in a case with containing the phase defect and the absorber pattern;

FIG. 7C is a diagram explaining a result obtained by observing a phase defect existing between absorber patterns adjacent to each other in observation of the EUVL mask having the absorber pattern according to the first embodiment of the present invention, and is a diagram illustrating light-intensity distribution of the dark-field inspection image in a case with containing only the absorber pattern;

FIG. 8A is a diagram explaining a result obtained by observing the phase defect existing between absorber patterns adjacent to each other in observation of the EUVL mask having the absorber pattern according to the first embodiment of the present invention, and is a diagram explaining a relationship between a pupil plane of the dark-field imaging optical system and diffracted light components from an edge of the absorber pattern;

FIG. 8B is a diagram explaining a result obtained by observing the phase defect existing between absorber patterns adjacent to each other in observation of the EUVL mask having the absorber pattern according to the first embodiment of the present invention, and is a diagram illustrating distribution of detection signal intensity obtained as a pixel signal column;

FIG. 9 is a process chart explaining a flow of a mask defect inspection according to the first embodiment of the present invention;

FIG. 10 is a diagram illustrating one example of a phase defect on a mask blank which is detected with using a method of inspecting a mask blank according to a second embodiment of the present invention;

FIG. 11A is a plan diagram of a principal part of a mask illustrating an example that the phase defect is completely covered by the absorber pattern, according to the second embodiment of the present invention;

FIG. 11B is a plan diagram of a principal part of a mask illustrating an example that the phase defect is not covered by the absorber pattern, according to the second embodiment of the present invention; and FIG. 12 is a process chart explaining a flow of a method of manufacturing the mask according to the second embodiment of the present invention.

DESCRIPTIONS OF THE PREFERRED EMBODIMENTS

In the embodiments described below, the invention will be described in a plurality of sections or embodiments when required as a matter of convenience. However, these sections or embodiments are not irrelevant to each other unless otherwise stated, and the one relates to the entire or a part of the other as a modification example, details, or a supplementary explanation thereof.

Also, in the embodiments described below, when referring to the number of elements (including number of pieces, values, amount, range, and the like), the number of the elements is not limited to a specific number unless otherwise stated or except the case where the number is apparently limited to a specific number in principle. The number larger or smaller than the specific number is also applicable. Further, in the embodiments described below, it goes without saying that the components (including element steps) are not always indispensable unless otherwise stated or except the case where the components are apparently indispensable in principle. Similarly, in the embodiments described below, when the shape of the components, positional relation thereof, and the like are mentioned, the substantially approximate and similar shapes and the like are included therein unless otherwise stated or except the case where it is conceivable that they are apparently excluded in principle. The same goes for the numerical value and the range described above.

Also, in some drawings used in the following embodiments, hatching is used even in a plan view so as to make the drawings easy to see. Further, in the following embodiments, the term "wafer" mainly indicates a silicon (Si) monocrystalline wafer and it indicates not only the same but also a silicon-on-insulator (SOI) wafer, an insulating film substrate for forming an integrated circuit thereon, or the like. The shape of the wafer includes not only a circular shape or a substantially circular shape but also a square shape, a rectangular shape, and the like.

Also, components having the same function are denoted by the same reference symbols throughout the drawings for describing the embodiments, and the repetitive description thereof is omitted. Hereinafter, the embodiments of the present invention will be explained in detail based on the drawings.

First Embodiment

Figure 1A:
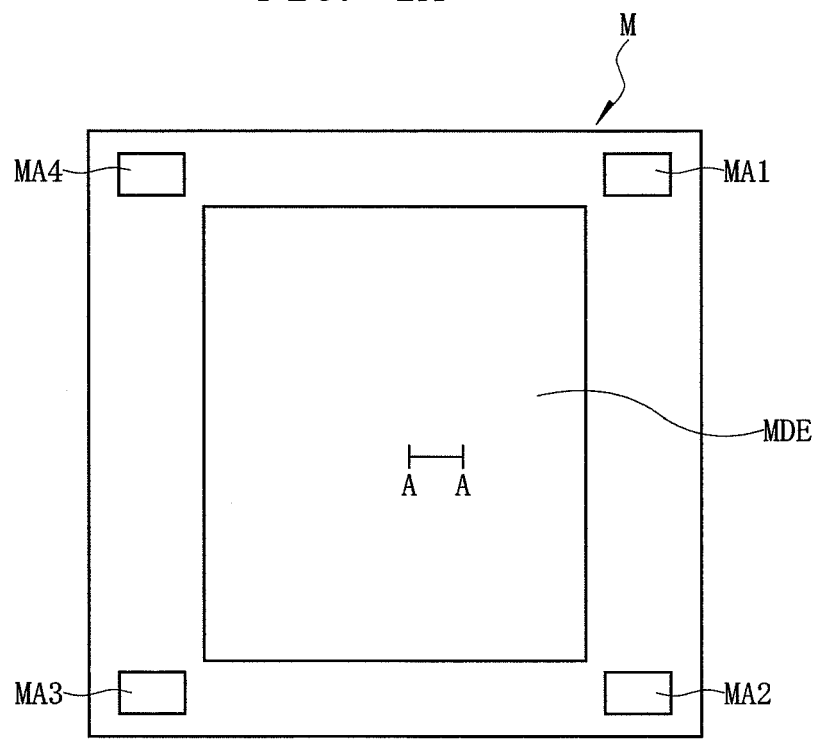
FIG. 1A is a plan view of a principal part of a plane on which an absorber pattern of an EUVL mask is formed, according to a first embodiment of the present invention.
Figure 1B:
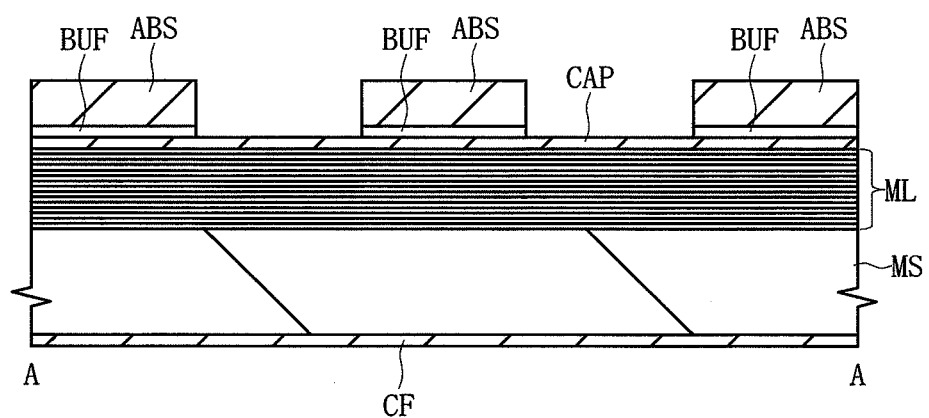
FIG. 1B is a cross-sectional view of a principal part illustrating an enlarged part along line A-A of FIG. 1A.

In order to clarify a purpose of a method of inspecting an EUVL mask according to a first embodiment, first, a structure of the EUVL mask and a structure of a projection optical system (a reduced projection optical system, a reflection-type exposure optical system, a reflection-type imaging optical system, and an EUV optical system) equipped in an EUVL exposure device will be explained with reference to FIGS. 1A, 1B, and 2. FIG. 1A is a plan view of a principal part of a plane on which an absorber pattern of the EUVL mask is formed, and FIG. 1B is a cross-sectional view of a principal part illustrating an enlarged part along line A-A of FIG. 1A. Also, FIG. 2 is a schematic diagram of the EUV projection exposure device.

As illustrated in FIG. 1A, a device pattern area "MDE" having a circuit pattern of a semiconductor integrated circuit device is provided in a center portion of an EUVL mask "M", and alignment mark areas "MA1", "MA2", "MA3", and "MA4" including a mark for positioning the EUVL mask M, a wafer alignment mark, and others are arranged in a peripheral portion thereof.

Also, as illustrated in FIG. 1B, a mask blank of the EUVL mask M includes: a substrate "MS" made of quartz glass or low thermal expansion glass; a multi-layered film "ML" obtained by alternately stacking molybdenum (Mo) and silicon (Si) (for example, about 40 layers are stacked for each of them) which are formed on a main plane of the substrate MS; a capping layer "CAP" formed on the multi-layered film ML; and a metal film "CF" for electrostatic chuck of the EUVL mask M formed on a rear plane of the substrate MS (a plane opposite to the main plane). A thickness of the substrate MS is, for example, about 7 to 8 mm, and a thickness of the multi-layered film ML is, for example, about 300 nm. Further, on the capping layer CAP, an absorber pattern "ABS" is formed via a buffer layer "BUF". A thickness of the absorber pattern ABS is, for example, about 50 to 70 nm.

Figure 2:
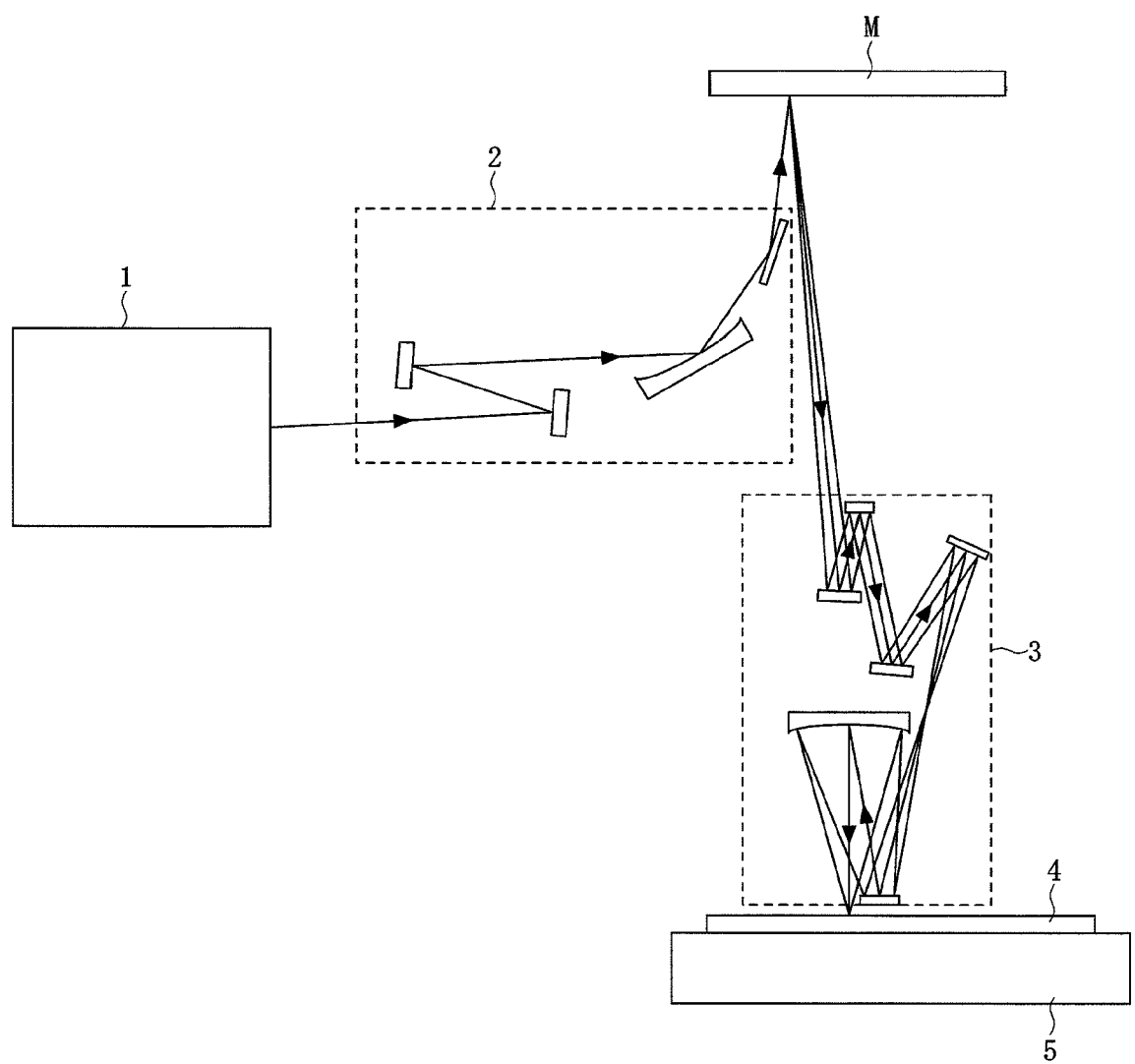
FIG. 2 is a schematic diagram of an EUV projection exposure device according to the first embodiment of the present invention.

Next, the EUV projection exposure device using the EUVL mask will be explained with reference to FIG. 2 illustrating its concept.

As illustrated in FIG. 2, the EUV light whose center wavelength is 13.5 nm and which is emitted from a light source 1 is irradiated through an illumination optical system 2 formed of a mirror reflector made of a multi-layered film to a plane (hereinafter, referred to as pattern plane) on which the absorber pattern of the EUVL mask is formed. The reflected light from the pattern plane passes through a reduced projection optical system 3 formed of a mirror reflector made of a multi-layered film, so that the pattern is transferred on a main plane of a wafer 4. Since the wafer is loaded on a stage 5, a lot of the patterns are transferred on a desirable region of the wafer 4 by repeating movement of the stage 5 and the pattern transfer.

Figure 3A:
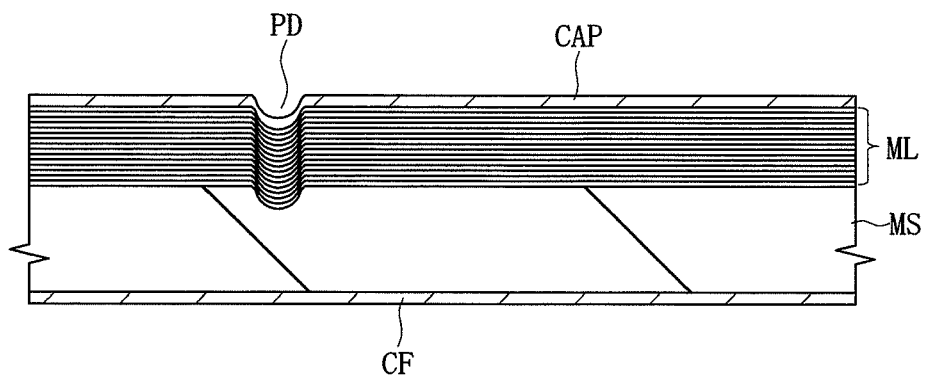
FIG. 3A is a cross-sectional view of a principal part of a mask blank having a phase defect, according to the first embodiment of the present invention.

Next, the phase defect caused in the mask blank of the EUVL mask will be explained with reference to FIGS. 3A and 3B. FIG. 3A is a cross-sectional view of a principal part of a mask blank having a phase defect, and FIG. 3B is a cross-sectional view of a principal part of the EUVL mask obtained by forming the absorber pattern and the buffer layer on the mask blank having the phase defect.

The cross-sectional view of the principal part of the mask blank illustrated in FIG. 3A illustrates one example that a concave-shaped phase defect "PD" is caused as a result of coating the above-described multi-layered film ML in a state that a micro void still exists in the main plane of the substrate MS when the multi-layered film ML is coated on the substrate MS.

Figure 3B:
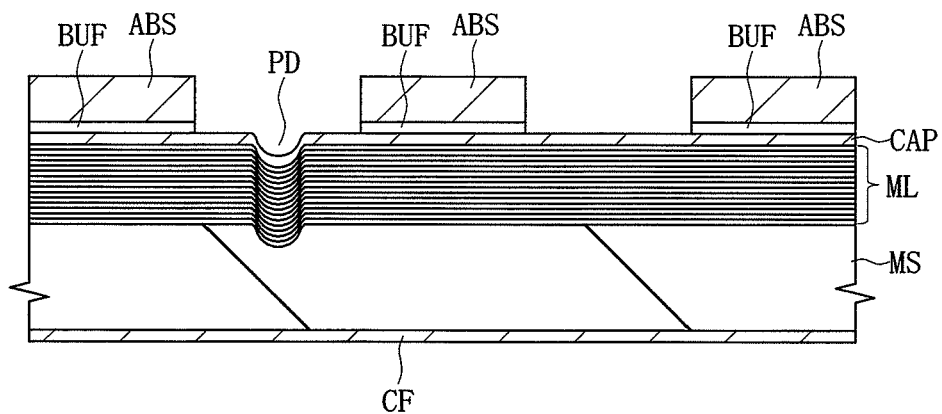
FIG. 3B is a cross-sectional view of a principal part of an EUVL mask obtained by forming an absorber pattern and a buffer layer on the mask blank having the phase defect, according to the first embodiment of the present invention.

If the buffer layer BUF and the absorber pattern ABS are formed in the state that this phase defect remains, the concave-shaped phase defect PD remains between the absorber patterns ABS adjacent to each other as illustrated in FIG. 3B. By the existence of the void of the phase defect PD of about 2 to 3 nm, a pattern projection image transferred on the main plane of the wafer in the EUVL is disturbed, a defect is caused in the transferred pattern on the main plane of the wafer. While FIGS. 3A and 3B illustrate one example of the void defect, a micro swell defect also causes the similar phase defect.

In a conventional photolithography mask, even if concavity/convexity of about several nm exists in a plane of a transparent mask blank, the concavity/convexity is ignorable. Therefore, there is a substantially-large difference in the defect transfer between the EUVL mask and the conventional photolithography mask. Therefore, in the EUVL mask, it is required to avoid the causing of the phase defect PD of the mask blank, which results in phase difference. Therefore, in the EUVL mask, it is required to detect the phase defect PD of the mask blank at a stage of the mask blank obtained prior to the formation of the absorber pattern ABS and the buffer layer BUF.

Figure 4:
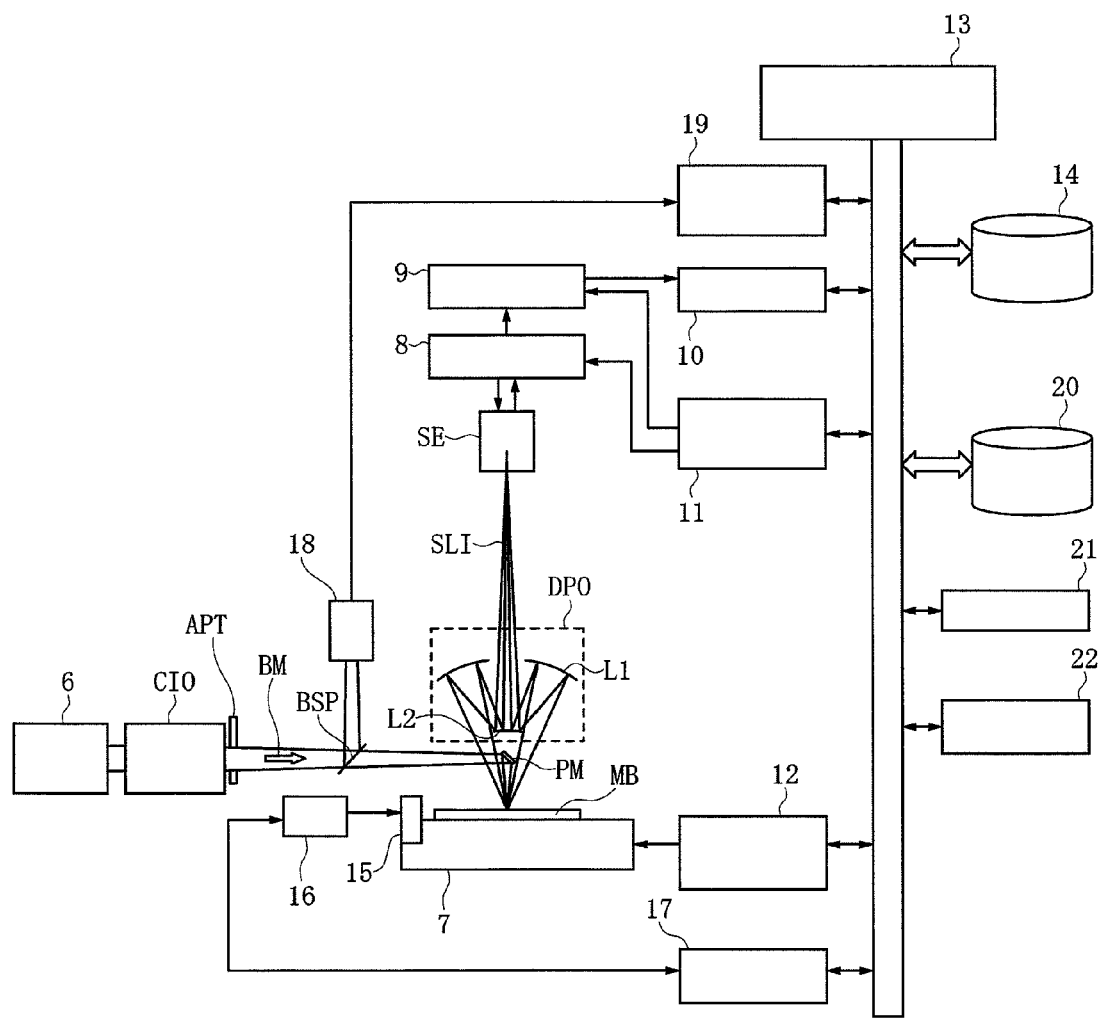
FIG. 4 is a schematic diagram illustrating an entire structure of a mask inspection device of collecting a dark-field inspection image of the mask blank or the EUVL mask with using EUV light, according to the first embodiment of the present invention.

Next, an entire structure of a mask inspection device according to the first embodiment will be explained with reference to FIG. 4. FIG. 4 is a schematic diagram illustrating the entire structure of the mask inspection device of collecting the dark-field inspection image of the mask blank or the EUVL mask with using EUV light. While the entire structure will be explained here with citing a mask inspection device used for inspecting the mask blank as an example, a mask inspection device with the similar structure is also used for the EUVL mask.

The mask inspection device includes: a light source (EUV light source, or plasma light source) 6 for generating EUV light (EUV inspection light, illumination light, or irradiation light) "BM"; a mask stage 7 for loading the mask blank MB thereon; an illumination optical system "CIO"; an imaging optical system "DPO"; a two-dimensional array sensor (image detector) "SE"; a sensor circuit 8; a pattern memory 9; a signal processing circuit 10; a timing controlling circuit 11; a mask-stage controlling circuit 12; a system controlling computer 13 for controlling operation of an entire device; and others. Also, it includes a data file 14 for storing various data related to a mask pattern.

The light source 6 includes a wavelength-selective filter, means for pressure bulkhead, means for suppressing dispersion particles, or others if required. The imaging optical system DPO includes a concave mirror "L1" and a convex mirror "L2", and is a Schwarzshild optical system configuring a dark-field imaging optical system having, for example, an outer NA (numerical aperture) of 0.2, an inner NA (which defines a light shielding portion at the center of pupil plane) of 0.1, and 26-fold magnification.

The mask blank MB for which the presence/absence of the phase defect is to be inspected is loaded on the mask stage 7 movable in three axis directions of X, Y, and Z. The EUV light BM whose center wavelength is 13.5 nm emitted from the light source 6 is converted through the illumination optical system CIO into convergent beam, and then, passes through an aperture unit "APT" for adjusting a beam size, is bent by a multi-layered mirror "PM", and is irradiated to a predetermined region of the mask blank MB. Here, the aperture unit APT plays a role of illumination aperture for changing the illumination NA, and a size of the aperture unit APT, that is, a size of the illumination aperture is controlled by an aperture driving unit (not illustrated) for adjusting the illumination aperture. A position of the mask blank MB is obtained as positional information of the mask stage 7 by reading a position of the mirror 15, which is fixed at the mask stage 7, with using a laser length-measuring machine 16. This positional information is transmitted to a position circuit 17, so that it can be recognized by the system controlling computer 13. Meanwhile, a part of the EUV light BM is branched by a beam splitter "BSP" to monitor light quantity by an EUV-light sensor 18, so that a threshold value for a signal processing can be set in an illumination intensity correcting circuit 19. This beam splitter BSP can be formed by a multi-layered film obtained by alternately stacking, for example, about several to ten pairs of molybdenum (Mo) and silicon (Si). The means for branching the part of the EUV light BM and guiding it to the EUV-light sensor 18 is not limited as the beam splitter BSP. For example, a multi-layered film mirror for reflecting only EUV light which is a part of a peripheral portion of light flux of the EUV light BM in a predetermined direction may be arranged, and the EUV light of the part may be guided to the EUV-light sensor 18.

The light scattered by the phase defect among the reflection light from the mask blank MB passes through the imaging optical system DPO to form convergent beam "SLI", and is collected to the two-dimensional array sensor (image detector) SE. That is, a dark-field inspection image of the mask blank MB is formed in the two-dimensional array sensor SE, and, as a result, the phase defect PD remaining in the mask blank MB is detected as a bright point in the inspection image. Information of a position of the detected phase defect PD, magnitude of a defect signal thereof, and others is memorized in a memory device 20, and besides, various types of information can be observed via a pattern monitor 21 or an image outputting unit 22.

Next, the method of inspecting the mask according to the first embodiment will be explained in detail.

<<Method of Inspecting Mask Blank>>

First, a relationship between the dark-field inspection image in the case that the phase defect exists in the mask blank and the scattered light passing through a pupil plane of the Schwarzschild optical system will be explained with reference to FIGS. 5A, 5B, and 5C.

FIG. 5A is an enlarged diagram of a part including the imaging optical system DPO and the mask blank MB illustrated in FIG. 4 described above. The EUV light BM is bent by the multi-layered film mirror PM, and is irradiated to a predetermined region of the mask blank MB. Among the light 30 reflected and scattered from the phase defect PD on the plane of the mask blank MB, the light proceeding toward a direction "31-1" of an annular region defined as a region inside the concave mirror L1 and outside the convex mirror L2 reflects on the concave mirror L1 to proceed in an inner direction indicated by a direction "31-2", and further reflects on the convex mirror L2 to proceed in one direction indicated by a direction "31-3", and proceed toward the two-dimensional array sensor SE.

FIG. 5B is a schematic diagram illustrating the pupil plane of the imaging optical system DPO according to the first embodiment. The annular region defined as the region from the inside of the concave mirror Li to the outside of the convex mirror L2 described in FIG. 5A above corresponds to a region between the outer NA (whose symbol is "NAOU") and the inner NA (whose symbol is "NAIN"). The inner NA (whose symbol is NAIN) corresponds to a region shielded by the convex mirror L2, and the convex mirror L2 is held by beams 32-1, 32-2, and 32-3. These beams 32-1, 32-2, and 32-3 are light-shielding substances against the scattered light passing through the imaging optical system DPO, and therefore, their shapes are thin, and they are provided at positions shifted from an X-direction axis (X axis) and a Y-direction axis (Y axis) so as not to shield the scattered light in only a specific direction. A symbol "NAILL" in the same drawing indicates the illumination NA obtained when the EUV light BM is irradiated to the EUVL mask.

FIG. 5C is a schematic diagram illustrating a pupil plane of an imaging optical system DPO including linear shielding portions according to the first embodiment. As illustrated in FIG. 5C, linear shielding portions 33-1, 33-2, 33-3, and 33-4 are provided along each of the X axis and the Y axis in the pupil plane of the imaging optical system DPO, and their widths W are set to be a smaller value than a diameter of the inner NA (whose symbol is NAIN). These linear shielding portions 33-1, 33-2, 33-3, and 33-4 may have a form allowed to be inserted or attached, or a form also including the beam structure for supporting the convex mirror L2.

A result obtained by observing the phase defect existing in the mask blank with using the dark-field imaging optical system having the pupil plane illustrated in FIG. 5B or the dark-field imaging optical system having the pupil plane illustrated in FIG. 5C will be explained with reference to FIGS. 6A and 6B. FIG. 6A is a diagram illustrating light-intensity distribution of a dark-field inspection image in a region where the phase defect exists, and FIG. 6B is a diagram explaining a relationship between pixel and the dark-field inspection image of the phase defect which is imaged on a light-receiving plane of the two-dimensional array sensor.

When the phase defect (corresponding to, for example, the phase defect PD illustrated in the above-described FIG. 3A) existing in the mask blank MB is observed with using the imaging optical system DPO explained with reference to the above-described FIGS. 5A to 5C, light-intensity distribution 34 of the dark-field inspection image as illustrated in FIG. 6A is obtained. Practically, signals obtained in the two-dimensional array sensor SE are obtained as not such a light-intensity distribution of the dark-field inspection image but a series of pixel light intensity stored for each pixel.

Here, when the mask blank MB is observed, the EUV light is irradiated to the mask blank MB, the EUV light having the illumination NA whose light flux is within the inner NA (whose symbol is NAIN) but larger than the widths W of the linear shielding portions in the pupil plane of the imaging optical system DPO illustrated in the above-described FIG. 5B or 5C, so that a contrast of the dark-field inspection image obtained as the pixel signal is improved.

FIG. 6B is a diagram explaining a relationship between the pixel and the dark-field inspection image with an enlarged image (light-intensity distribution 34) of the phase defect which has been magnified 26 times to be imaged on the light-receiving plane of the two-dimensional array sensor SE. In the drawing, a symbol "Pxy" indicates a size of one side of the pixel, a symbol 35 indicates a boundary between the pixels, a symbol 36 indicates a pixel with the enlarged image of the phase defect, and a symbol 37 indicates a pixel without the enlarged image of the phase defect. The light quantity stored in the pixel 36 with the enlarged image (light-intensity distribution 34) of the phase defect is more than the light quantity stored in the pixel 37 without the enlarged image of the phase defect, and therefore, a position of the pixel with the phase defect can be specified.

<<Method of Inspecting EUVL Mask>>

Next, in observation of the EUVL mask M having the absorber pattern, a result obtained by observing a phase defect (corresponding to, for example, the phase defect PD illustrated in FIG. 3B described above) existing between the absorber patterns adjacent to each other will be explained with reference to FIGS. 7A, 7B, 7C, 8A, and 8B. FIG. 7A is an enlarged diagram of a part including the imaging optical system DPO and the EUVL mask M illustrated in the above-described FIG. 4 (diagram explaining a relationship between the dark-field imaging optical system and the EUV light diffracted from the absorber pattern), FIG. 7B is a diagram illustrating light-intensity distribution of the dark-field inspection image in the region where the phase defect exists in the case with the phase defect and the absorber pattern, and FIG. 7C is a diagram illustrating light-intensity distribution of the dark-field inspection image in the case with only the absorber pattern. Also, FIG. 8A is a diagram explaining a relationship between the pupil plane of the imaging optical system DPO and diffracted-light components from an edge of the absorber pattern, and FIG. 8B is a diagram illustrating intensity distribution of a detection signal obtained as a pixel signal column.

As illustrated in FIG. 7A, as the light reflected from the pattern plane of the EUVL mask M, high-order diffracted-light components 38 and 39 caused depending on periodicity of the absorber pattern in addition to the scattered light caused by the phase defect are captured by the concave mirror L1 to form the dark-field inspection image on the light-receiving plane of the two-dimensional array sensor SE. As a result, as illustrated in FIG. 7B, light-intensity distribution 40 of the dark-field inspection image of the phase defect and diffracted-light intensity distribution 41 from the edge of the absorber pattern are obtained. FIG. 7C illustrates the light-intensity distribution of the dark-field inspection image obtained in a case that only the diffracted-light components from the edge of the absorber pattern are obtained without the dark-field inspection image of the phase defect.

Here, when the EUVL mask M is observed, the EUV light is irradiated to the EUVL mask M, the EUV light having the illumination NA whose light flux is as large as or smaller than the thicknesses (widths) of the linear shielding portions provided along each of the X axis and the Y axis in the pupil plane of the imaging optical system DPO illustrated in the above-described FIG. 5C.

FIG. 8A is a diagram explaining a relationship between the pupil plane of the imaging optical system DPO and diffracted-light components from the edge of the absorber pattern. A circular region 43-1 indicates a size of the illumination NA and a region size to which a zero-order reflection component reaches from the pattern plane of the EUVL mask M, and is shielded by the center shielding portion. Further, the linear shielding portions shield most of a first-order diffracted-light component 43-2, a second-order diffracted-light component 43-3, a third-order diffracted-light component 43-4, a fourth-order diffracted-light component 43-5, a minus first-order diffracted-light component 43-6, a minus second-order diffracted-light component 43-7, a minus third-order diffracted-light component 43-8, and a minus fourth-order diffracted-light component 43-9 from the edge of the absorber pattern.

As a result, in a detection signal 45 obtained in the case with the linear shielding portions as compared to a detection signal 44 obtained in the case without the linear shielding portion as illustrated in FIG. 8B, while an intensity level of the signal is lowered, the signal is detected as a pixel signal whose intensity of the pixel with the phase defect is relatively brighter than that in the periphery thereof. That is, in the detection signal 45 obtained in the case with the linear shielding portions, the pixel signal without the phase defect has a sufficient small value, and therefore, the contrast of the detected image is improved.

Each pattern of most of semiconductor devices has basically a pattern group arranged in an X direction and a Y direction. Therefore, it is sufficient to arrange the above-described linear shielding portions along both directions of the X and Y directions of the pupil plane of the imaging optical system DPO.

When the illumination NA is set as large as the inner NA similarly to the case of the mask blank inspection, the high-order diffracted-light component cannot be shielded by the linear shielding portions, and passes through the pupil plane of the imaging optical system DPO, and, as a result, the contrast of the dark-field inspection image obtained as the pixel signal is lowered. However, by narrowing the illumination NA, the contrast of the dark-field inspection image can be improved, and the phase-defect detection with high sensitivity can be performed.

A flow of the mask defect detection according to the first embodiment described above will be explained with reference to the above-described inspection device illustrated in FIG. 4 and a flowchart illustrated in FIG. 9.

<Step S101>

First, the mask blank or the EUVL mask which is a sample to be inspected is loaded on the stage 7 of the inspection device. The reference mark on the EUVL mask is read if required to position the stage 7 by the mask-stage controlling circuit 12. This position is read by a laser length-measuring machine (laser interferometer) 16, and is memorized as a reference coordinate on the EUVL mask.

<Step S102>

The information of the sample to be inspected, that is, information of determining the mask blank obtained prior to the formation of the absorber pattern or the EUVL mask having the absorber pattern (mask with the absorber pattern) is inputted. In the case of the EUVL mask, if it is known that a region to be inspected is limited, information of the inspection region is also inputted if required.

<Steps S103 to S104>

In the case that the sample to be inspected is the mask blank, the illumination aperture for defining the illumination NA of the EUV light, that is, the aperture APT is controlled by the aperture driving unit so as to set the illumination NA to be within the inner NA but a larger value, and the light is irradiated to the mask blank.

<Step S105>

Then, the phase defect is detected over the whole plane of the mask blank, and the positional information and the signal intensity information of the detected phase defect are memorized. The positional information of the phase defect can be calculated from positional information of the pixel at which the signal with the phase defect is obtained.

<Step S106>

Further, a number is provided to the signal intensities in a descending order, and this is also memorized as the priority order indicating the degree of the influence of the phase defect on the transfer pattern.

<Steps S103 to S107>

On the other hand, in the step of S103, in the case that the sample to be inspected is the EUVL mask having the absorber pattern, the aperture APT for defining the illumination NA of the EUV light is controlled to set the illumination NA so as to be a sufficiently smaller value than the inner NA and as large as (see FIG. 5C described above) or smaller than the widths of the linear shielding portions, and the light is irradiated to the EUVL mask.

<Step S108>

Within the region to be inspected, which has been previously inputted, the phase defect of the EUVL mask is detected. Even if the phase defect exists at the stage of the mask blank, this does not substantially become the defect as long as the phase defect is covered by the absorber pattern, and therefore, the detection signal of the phase defect is not obtained.

<Step S109>

The information of the remaining phase defect (which is the phase defect not covered by the absorber pattern and substantially affecting the pattern transfer) is memorized. If the phase defect is covered by the absorber pattern, the detection signal of the phase defect is not obtained at this moment. If it is not covered, it is detected as the phase defect remaining in the EUVL mask.

As described above, according to the first embodiment, the phase defect remaining in the reflection plane of the multi-layered film can be detected at the high detection sensitivity in both of the mask blank obtained prior to the formation of the absorber pattern and the EUVL mask having the absorber pattern.

Second Embodiment

In a second embodiment, a method of manufacturing the EUVL mask including the step of inspecting the phase defect of the mask blank and the step of inspecting the phase defect remaining in the EUVL mask explained in the above-described first embodiment will be explained, and the method is capable of apparently reducing or eliminating the influence of the phase defect by adjusting a shape of the absorber pattern in the periphery of the phase defect when it is determined that the remaining phase defect affects the transfer of the absorber pattern.

First, a mask blank MB is prepared. FIG. 10 is a diagram illustrating one example of the phase defect on the mask blank MB detected by the defect inspection for the mask blank which has been explained in the above-described first embodiment. The phase defects 46-1, 46-2, 46-3, and 46-4 are defects critically affecting when the absorber pattern formed on the mask blank MB is transferred on the main plane of the wafer by the projection exposure device, and are phase defects to which the high priority order is provided. On the other hand, the phase defects 47-1, 47-2, and 47-3 are phase defects to which the low priority order is provided. For all of these phase defects, their positions are obtained in a coordinate system defined by reference marks 48-1, 48-2, 48-3, and 48-4 provided on the mask blank MB.

Next, the absorber pattern is formed on the mask blank MB to form the EUVL mask. Finally, the structure of the EUVL mask becomes the same structure illustrated in FIG. 1 in the above-described first embodiment. At this time, in order to cover the above-described phase defects to which the high priority-order numbers are provided by the absorber pattern as completely as possible, a position at which the absorber pattern is to be formed is determined with respect to the reference marks 48-1, 48-2, 48-3, and 48-4 to form the absorber pattern.

One example of the defects is illustrated in FIGS. 11A and 11B. FIG. 11A is a plan view of a principal part of a mask illustrating an example that both of phase defects 51-1 and 51-2 having the high priority order are completely covered by the absorber pattern ABS. That is, the phase defects disappear on the EUVL mask. On the other hand, FIG. 11B is a plan view of a principal part of a mask illustrating an example that both of the phase defects 51-1 and 51-2 are not covered by the absorber pattern ABS and remain in the EUVL mask. If the positioning failure occurs in the formation of the absorber pattern, the defect having even the high priority order cannot be covered by the absorber pattern ABS in some cases.

By the inspection device using the EUV light as the inspection light, it is verified whether the phase defect is covered or not in the EUVL mask on which such an absorber pattern is formed. More particularly, the inspection method for the EUVL mask described in the first embodiment above is effective. At this time, as the inspection region of the EUVL mask, even a narrow region including the position at which the phase defect has been detected in the above-described inspection for the mask blank is sufficient to be inspected. Although the handling of the remaining phase defect is a problem, it is considered that, for example, the phase defect 52-1 has small influence because of sufficiently far from the absorber pattern. If the influence is large, the absorber pattern is locally formed for only the phase defect, so that the influence of the phase defect can be reduced.

Also, regarding the phase defect 52-2 remaining between the absorber patterns adjacent to each other, the influence in the pattern transfer by the exposure device can be reduced by the method disclosed in, for example, Japanese Patent Application Laid-Open Publication No. 2002-532738 (Translation of PCT Application) (Patent Document 4), that is, by adjusting the contour of the absorber pattern adjacent to the phase defect.

If the influence of the phase defect cannot be reduced even by the formation of the absorber pattern or the adjustment of the contour described above, the EUVL mask is a defective product. However, in most cases, the critical phase defect is covered by the absorber pattern, and therefore, the influence of the phase defect remaining in the EUVL mask can be sufficiently reduced.

A flow of the method of manufacturing the mask according to the second embodiment described above will be explained with reference to a flowchart illustrated in FIG. 12.

<Step S201>
First, a mask blank obtained by coating a multi-layered film and a capping layer on a substrate is prepared.

<Step S202>
The mask blank is inspected with using the inspection method which has been explained in the above-described first embodiment.

<Steps S203 to S204>
In the case that the phase defect exists in the mask blank, simultaneously with the provision of the priority order to the detected phase defect, the priority order and the positional coordinate (defect coordinate) of the phase defect with respect to the predetermined reference mark are memorized.

<Step S205>
The absorber pattern is formed on the mask blank. At this time, the position of the absorber pattern is calculated so as to cover the above-described phase defect having the high priority order by the absorber pattern as completely as possible to form the pattern.

<Step S206>
The defect inspection for the absorber pattern is performed. If the phase defect exists in the absorber pattern, the portion to be adjusted and an adjustment degree are separately calculated.

<Step S207>
The EUVL mask having the absorber pattern is inspected with using the inspection method which has been explained in the above-described first embodiment. In this inspection, the inspection over the whole plane of the EUVL mask is not always necessary, and the inspection may be performed for limited regions which are the positional coordinate of the phase defect memorized as having the priority order in the step of S204 and a periphery of the position.

<Steps S208 to S209>
If it is determined that the critical phase defect remains in the EUVL mask as a result of the inspection in the step of S207, a local portion to be adjusted of the above-described absorber pattern and an adjustment degree are calculated in order to reducing the influence of the phase defect.

<Steps S212 to S213>
After finishing the above-described steps, if the portion to be adjusted exists in the absorber pattern, the above-described local absorber pattern is adjusted. It is accordingly checked whether the adjustment has been appropriately performed or not, by performing the inspection using the EUV light as the inspection light again, performing a practical exposure evaluation, or others. By the above-described step, steps of manufacturing the EUVL mask are finished.

<Steps S203 to S210>

On the other hand, in the step S203, if it is determined that the phase defect does not exist in the mask blank, the absorber pattern is formed by the usual steps to manufacture the EUVL mask.

<Step S211>

Then, the conventional defect inspection for the absorber pattern is performed. If the phase defect exists in the absorber pattern, the portion to be adjusted and an adjustment degree are separately calculated. Hereinafter, the process moves to the step of S212 followed by the above-described same steps, and steps of manufacturing the EUVL mask are finally finished.

As described above, by the method of manufacturing the mask according to the second embodiment, the phase defect substantially existing in the manufactured EUVL mask can be significantly reduced, and besides, the defect of the pattern projection image caused by the phase defect remaining in the multi-layered film of the EUVL mask can be recovered by the adjustment of the absorber pattern. As a result, even if the phase defect exists in the mask blank, the defect is substantially not defective at the stage of the completion of the EUVL mask, so that frequency of a state that this is available as a non-defective product is increased. Therefore, a manufacture yield of the EUVL mask can be significantly improved, and this can contribute to cost reduction of the EUVL mask.

In the foregoing, the invention made by the inventors has been concretely described based on the embodiments. However, it is needless to say that the present invention is not limited to the foregoing embodiments and various modifications and alterations can be made within the scope of the present invention.

The present invention can be applied to a method of inspecting an EUVL mask using EUV light as inspection light, to an inspection device, and to a method of manufacturing the EUVL mask.

What is claimed is:

1. A method of inspecting a mask for reflecting extreme ultra-violet ("EUV") light, comprising the steps of:
    (a) irradiating the EUV light to the mask;
    (b) imaging the EUV light which reflects from the mask onto a light-receiving plane of an image detector through a dark-field imaging optical system to form a dark-field inspection image on the light-receiving plane; and
    (c) detecting a detection signal of a phase defect existing in the mask from detection signals obtained by the image detector, and
    the step (a) further including the steps of:
    (a1) inputting information indicating whether an absorber pattern exists or not in an inspection region of the mask; and
    (a2) changing an illumination numerical aperture ("NA") of the EUV light with which the mask is irradiated, depending on either a case that the absorber pattern exists or a case that the absorber pattern does not exist.

2. The method of inspecting a mask according to claim 1, wherein the dark-field imaging optical system includes a magnifying optical system including a plurality of reflection mirrors made of a multi-layered film, and a pupil plane of the dark-field imaging optical system includes: a center shielding portion for shielding the EUV light arranged at a center of the pupil plane; and linear shielding portions for shielding the EUV light respectively arranged along an X axis and a Y axis orthogonal to the X axis and each having a smaller width than a diameter of the center shielding portion,
in the case that the absorber pattern does not exist, the phase defect existing in the mask is detected by irradiating the EUV light having illumination NA within an inner NA but larger than the widths of the linear shielding portions, and,
in the case that the absorber pattern exists, the phase defect existing in the mask is detected by irradiating the EUV light having illumination NA as large as or smaller than the widths of the linear shielding portions.

3. A mask inspection device comprising:
a stage movable in an X direction and a Y direction orthogonal to the X direction, on which a mask having an absorber pattern is loaded;
a light source which generates extreme ultra-violet ("EUV") light;
an illumination optical system to irradiate the EUV light to the mask;
illumination aperture to change an illumination numerical aperture ("NA") of the EUV light irradiated to the mask;
a dark-field imaging optical system to collect scattered light from the mask and form a dark-field inspection image;
an image detector to acquire the dark-field inspection image as a pixel signal; and
an aperture driving unit to adjust the illumination aperture based on information of the absorber pattern.

4. The mask inspection device according to claim 3, wherein a pupil plane of the dark-field imaging optical system includes: a center shielding portion for shielding the EUV light arranged at a center of the pupil plane; and linear shielding portions for shielding the EUV light respectively arranged along an X axis and a Y axis orthogonal to the X axis and each having a smaller width than a diameter of the center shielding portion.

* * * * *